(12) United States Patent
Mansfield et al.

(10) Patent No.: US 10,324,101 B1
(45) Date of Patent: Jun. 18, 2019

(54) HVI SAMPLE FEED KIT

(71) Applicant: Quantitative Engineering Solutions, LLC, Farragut, TN (US)

(72) Inventors: Joe Mansfield, Knoxville, TN (US); Clark A. Roberts, Maryville, TN (US)

(73) Assignee: Quantitative Engineering Solutions, LLC, Knoxville, TN (US)

( * ) Notice: Subject to any disclaimer, the term of this patent is extended or adjusted under 35 U.S.C. 154(b) by 344 days.

(21) Appl. No.: 15/142,700

(22) Filed: Apr. 29, 2016

Related U.S. Application Data (60) Provisional application No. 62/154,856, filed on Apr. 30, 2015.

(51) Int. Cl.
| | |
|---|---|
| *G01N 1/00* | (2006.01) |
| *G01N 1/04* | (2006.01) |
| *G01N 1/22* | (2006.01) |
| *D01G 23/04* | (2006.01) |
| *D01G 23/08* | (2006.01) |
| *G01N 35/00* | (2006.01) |
| *G01N 35/10* | (2006.01) |

(52) U.S. Cl.
CPC .............. *G01N 35/10* (2013.01); *D01G 23/04* (2013.01); *D01G 23/08* (2013.01); *G01N 1/04* (2013.01); *G01N 1/2202* (2013.01); *G01N 2001/002* (2013.01); *G01N 2035/00465* (2013.01)

(58) Field of Classification Search
CPC ........ D01G 23/08; D01G 23/04; G01N 35/10; G01N 2001/002; G01N 1/04
See application file for complete search history.

(56) References Cited

U.S. PATENT DOCUMENTS

| | | | |
|---|---|---|---|
| 4,470,172 A * | 9/1984 | Leifeld ................. | D01G 23/08 19/105 |
| 5,892,142 A | 4/1999 | Ghorashi et al. | |
| 6,098,454 A | 8/2000 | Ghorashi et al. | |
| 6,161,441 A | 12/2000 | Ghorashi et al. | |
| 6,341,806 B1 | 1/2001 | Chung | |
| 2014/0096623 A1* | 4/2014 | Mansfield ............... | G01N 1/04 73/863.21 |

* cited by examiner

*Primary Examiner* — Paul M. West
(74) *Attorney, Agent, or Firm* — Knox Patents; Thomas A. Kulaga (57) ABSTRACT

Apparatus for automating a high volume instrument (HVI) used for the classification of all Upland and American Pima cotton, including determining trash and color. A sub-sample delivery tube sub-system and a sample drum air chamber sub-system allow the HVI to receive sub-samples from an automated cotton system. A delivery tube, with an air dissipater, delivers the automated sub-sample to the HVI sample drum while an air chamber below the sample drum applies a negative air pressure to the drum. A sub-sample air-knife extraction sub-system and an autoMIC transfer tube assist sub-system allow the HVI to release automated sub-samples after the sample drum in the HVI has completed its operations on the sub-sample. An air-knife applies air jets to the sample plate of the HVI sample drum to release the sub-sample. As the sub-sample leaves the drum an air jet is actuated to push the sub-sample along a transfer tube.

18 Claims, 6 Drawing Sheets

HVI SAMPLE FEED KIT

CROSS-REFERENCE TO RELATED APPLICATIONS

This application claims the benefit of U.S. Provisional Application No. 62/154,856, filed Apr. 30, 2015.

STATEMENT REGARDING FEDERALLY SPONSORED RESEARCH OR DEVELOPMENT

Not Applicable

BACKGROUND

1. Field of Invention

This invention is for an automated HVI system. More particularly, this invention pertains to additions to a manually operated High Volume Instrument (HVI), which is an instrument used for the classification of all Upland and American Pima cotton, including determining trash and color. The additions include a sub-sample delivery sub-system, a sample drum air chamber sub-system, a sub-sample air knife sub-system, and an automatic Micronaire transfer tube assist sub-system.

2. Description of the Related Art

High volume instruments (HVI) are used for the classification of all Upland and American Pima cotton, including determining trash and color. One type of high volume instrument (HVI) has been a manually operated test instrument manufactured for several decades by Uster Technologies. The manual portion of the instrument requires manually-separating a sub-sample from a primary sample of cotton, placing the sub-sample into the instrument, and initializing testing by depressing a start button.

A human can pull one clump of sub-sample from a primary sample while a Cotton Acquisition and Tracking System (CATS) pulls several tufts with a card wheel and accumulates them in a tube. An example of a CATS is disclosed in U.S. Published Application Number 2014/0096623, titled "Cotton acquisition and tracking system." The automated creation of the sub-sample creates a different sub-sample, one with less cohesiveness than a hand-pulled sub-sample.

Over the evolution of the HVI several new technologies and safety improvements have been designed and implemented within the instrument without regard to any non-manually loaded sub-sample configuration. That is, the sub-sample is assumed to be a single cohesive clump versus a fluffy sub-sample that is made of several smaller tufts, such as delivered by CATS. Specifically, a few of the new technologies which are the most problematic for fluffy, non-cohesive, automatically placed sub-samples include 1) a light curtain that ensures nothing is in the proximity of the instrument's sample drum before testing begins; 2) an automatic Micronaire (AutoMic) test on one of the two aforementioned sub-samples, requiring that the sub-sample be automatically transported within the HVI from the sample drum to the new test device; and 3) a sub-sample transport device that transfers a particular sub-sample from the sample drum via a funnel and transfer tube type system utilizing compressed air.

BRIEF SUMMARY

According to one embodiment of the present invention, a sample feed kit adapted to fit a High Volume Instrument (HVI) is provided. An HVI, such as the one sold by Uster, is configured for manual insertion of the cotton sample for testing. In its standard configuration the HVI is not suitable for automatic operation. The HVI sample feed kit automates the manual HVI by providing a sub-sample delivery tube sub-system, a sample drum air chamber sub-system, a sub-sample air-knife sub-system, and an automatic Micronaire (autoMIC) transfer tube assist sub-system.

In an automated cotton sampling system, sub-samples are delivered to the HVI via a pneumatic system. Such automated cotton sampling systems are disclosed in U.S. U.S. Published Application Number 2014/0096623, titled "Cotton acquisition and tracking system," filed on Oct. 8, 2013, and U.S. patent application Ser. No. 14/690,299, filed on Apr. 17, 2015, both of which are hereby incorporated by reference. The HVI is configured to receive the cotton sample as a clump manually extracted and inserted into the HVI. In an automated system, the automated sub-sample is collected and delivered to the HVI through a pneumatic system. The automated sub-sample is a loose collection of fibers extracted from a sample obtained from a bale.

An advantage of the sample feed kit is that automated insertion of non-cohesive sub-samples resolves the issues in the HVI that would otherwise have negative effects on instrument reliability, data product quality, production efficiency, and, ultimately, increased operational costs. One such issue is that blowing non-cohesive sub-samples into the sample drum is like blowing leafs into a pile—some of the leaves do not make it into a nice pile. These errant tufts of cotton that do not stay in the sample drum block safety sensors, jam moving mechanisms, and create other problems. These errant puffs result in the instrument stopping due to errors and service technicians interactions to clear the errant cotton. A second issue is that errant sample tufts amass over a short period creating a mess of cotton, both in and out of the instrument. These masses of errant sample tufts result in significantly more periodic cleaning.

A third issue is that the autoMIC measurement requires a certain defined mass range of sub-sample. If CATS successfully acquires that required mass of sub-sample, but ultimately that exact mass never makes it into the test mechanism (because all of the cotton is not contained in and then released from the sample drum), the odds are high that the test will not have enough sample mass for adequate data product. If the test mechanism determines there is not adequate mass for the test, the HVI rejects that sub-sample and the instrument's production efficiency is negatively affected. Another issue is that an automated sub-sample is difficult to puff out of the sample drum because it is non-cohesive, although a manually placed sub-sample moves easily through the transport mechanism.

The sample feed kit includes four sub-systems that address the above issues and allows for automated use of an HVI. The sub-systems are adapted to attach to the HVI. They include a sub-sample delivery tube sub-system, a sample drum air chamber sub-system, a sub-sample air-knife extraction sub-system, and an autoMIC transfer tube assist sub-system.

The sub-sample delivery tube emulates the manual placement of the sub-sample into the instrument by blowing the cotton sub-sample through a large tube which forces the sub-sample into the instrument's sample drum. Without the delivery tube, the delivery of the automated sub-sample is problematic. The sub-sample delivery tube sub-system includes a cylindrical pipe angled to deliver the sub-sample directly into the receiving chamber of the HVI sample drum. The angle of entry is controlled. For example, in one embodiment the angle of entry is 22.5 degrees. In one embodiment, the terminal end of the pipe includes a series of holes that dissipate the air pressure driving the sub-sample such that the sub-sample velocity drops before entry into the HVI drum and the amount of air following the sub-sample into the sample drum is minimized.

The sample drum air chamber sub-system aids the sample drum in receiving the sub-sample. The sample drum air chamber mates to the HVI frame under the sample drum and provides vacuum suction when the sub-sample is delivered to the sample drum.

The sub-sample air-knife extraction sub-system aids in the removal of the sub-sample from the sample drum after the sub-sample is processed in the sample drum. The sub-sample air-knife includes a curved and multi-ported air nozzle configured to push the sub-sample away from the sample drum's sample plate.

The autoMIC transfer tube assist sub-system aids in the transfer of the sub-sample after the sub-sample is processed in the sample drum. The autoMIC transfer tube includes an air jet triggered at the same time as the air-knife. The air jet assists the sub-sample transfer to the Micronaire testing portion of the HVI.

BRIEF DESCRIPTION OF THE SEVERAL VIEWS OF THE DRAWINGS

The above-mentioned features will become more clearly understood from the following detailed description read together with the drawings in which.

DETAILED DESCRIPTION

Apparatus for an automated HVI system 100 is disclosed. The automated HVI system 100 includes a sub-sample delivery nozzle or tube sub-system 106, a sample drum air chamber sub-system 108, a sub-sample air knife sub-system 110, and an autoMIC transfer tube assist sub-system 112.

Figure 1:
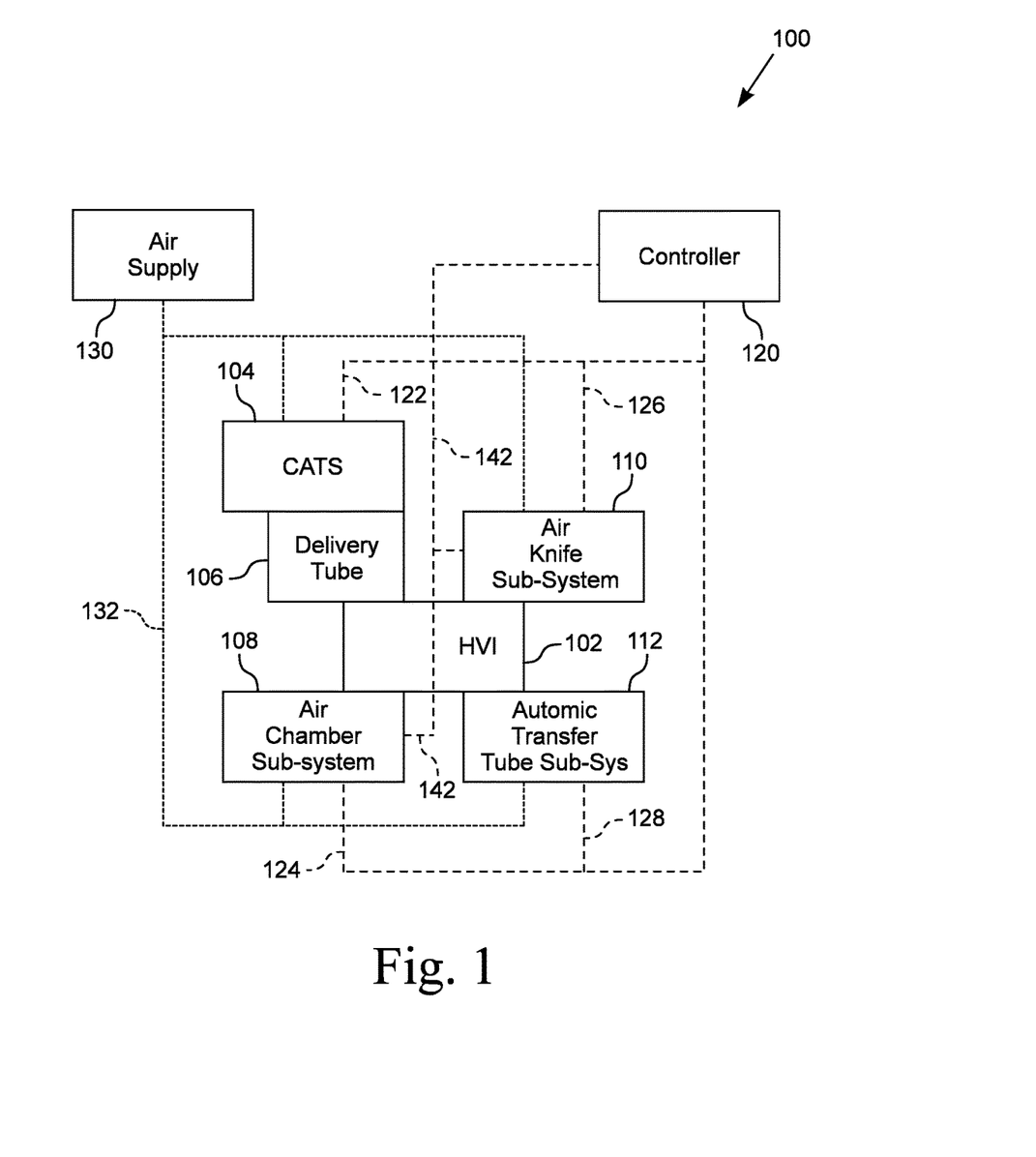
FIG. 1 is a block diagram of one embodiment of an automated HVI system.

FIG. 1 illustrates a block diagram of one embodiment of an automated HVI system 100. The conventional High Volume Instrument (HVI) 102 is configured for manual insertion of cotton samples. The illustrated embodiment shows a Cotton Acquisition and Tracking System (CATS) 104, which is an automated system for cotton classing operations that includes obtaining sub-samples 204 from primary cotton samples and transporting those sub-samples 204 to selected test devices, such as the HVI 102. In other embodiments, the cotton sub-samples 204 are sampled and transported either manually or with a system other than CATS 104. A sub-sample delivery tube sub-system 106 transports sub-samples 204 from the CATS 104 or other conveying system to the HVI 102. An air chamber sub-system 108 is attached to the HVI 102 to aid in the delivery of the sub-sample 204 to the sample drum 202 in the HVI 102.

After a sub-sample 204 is processed by the HVI 102 in the sample drum 202, the sub-sample 204 is transported to the autoMIC device for Micronaire testing. An air-knife sub-system 110 directs multiple air steams, or jets of air, 234 to release the sub-sample 204 from the sample drum 202 and an autoMIC transfer tube sub-system 112 aids in moving the released sub-sample 204 to the autoMIC in the HVI 102.

The automated HVI system 100 is a pneumatic system that uses air pressure to aid in the transport of the sub-sample 204. An air supply 130 provides air pressure to the system 100 through air supply lines 132 to the CATS 104, air chamber sub-system 108, air-knife sub-system 110, and autoMIC transfer tube sub-system 112. The application of air pressure from the air supply 130 is controlled by a controller 120. The controller 120 is responsive to signals 142 from sensors in the system 100. The controller 120 provides control signals 122, 124, 126, 128 to the various sub-systems 104, 108, 110, 112.

Figure 2:
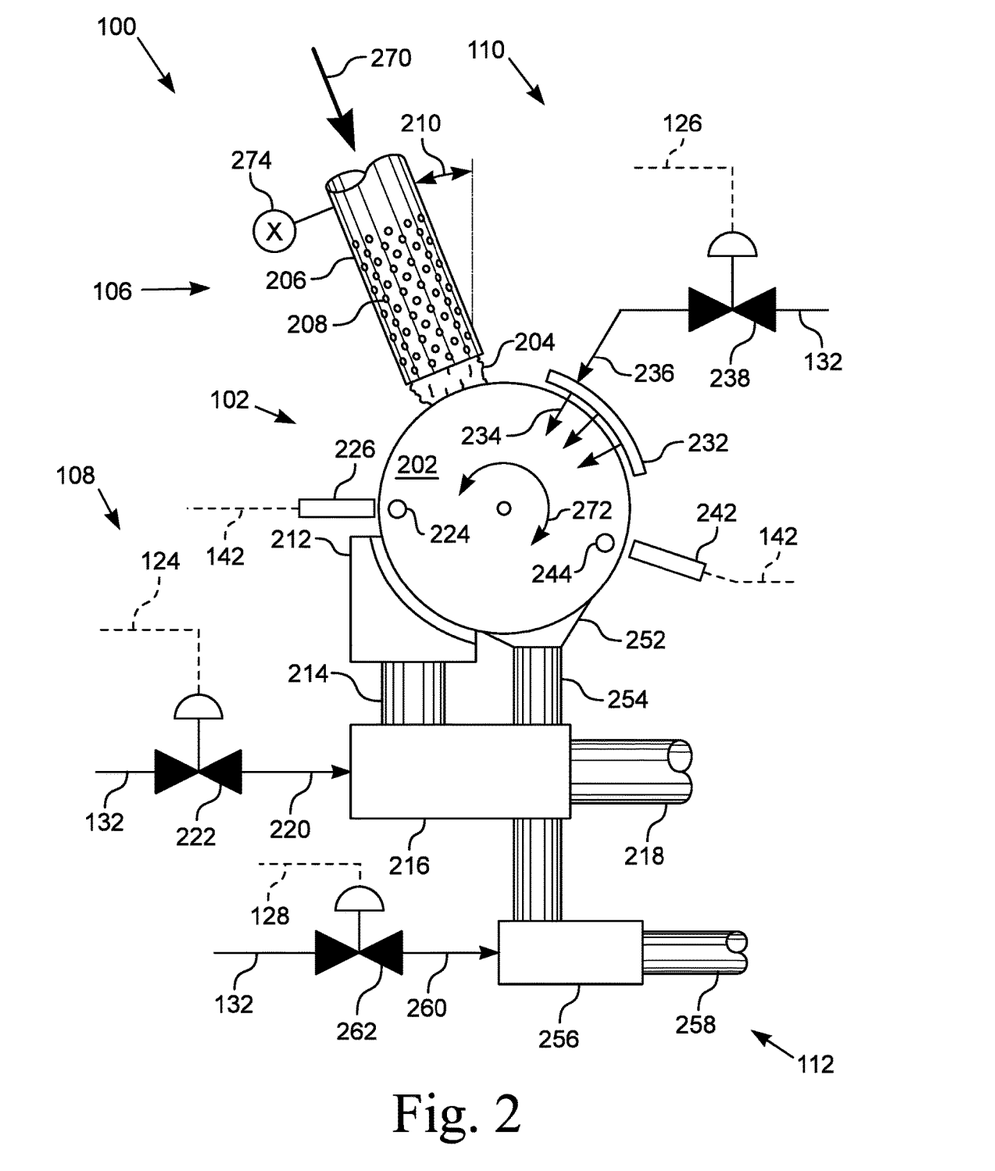
FIG. 2 is a symbolic diagram of one embodiment of a HVI sample feed kit attached to an HVI sample drum.

FIG. 2 illustrates a symbolic diagram of one embodiment of a HVI sample feed kit attached to an HVI sample drum 202. The sample drum 202 reciprocates 272 rotationally on its axis. The HVI 102 includes a sample drum 202 with a chamber that receives the sub-sample 204 from the delivery tube 206. The sample drum 202 includes a sample plate on its outer circumference. The sample plate has a series of holes through-which the sub-sample 204 protrudes. In this way the HVI 102 obtains fibers for HVI testing. The sample drum 202 rotates in order to perform its functions within the HVI 102.

The sub-sample delivery tube sub-system 106 delivers a sub-sample 204 to the sample drum 202. The delivery tube sub-system 106 includes a pipe or tube 206 that terminates next to the sample drum 202. In one embodiment, the gap between the end of the delivery pipe 206 and the opening in the sample drum 202 is sufficient to aid in dissipating the air stream 270 pushing the sub-sample 204 through the pipe 206. In one embodiment, the delivery tube 206 is a clear acrylic, large diameter tube that allows the sub-sample 204 to be visible as it traverses the tube 206.

The tube 206 is oriented at an angle 210 from vertical that ensures delivery of the sub-sample 204 to the drum 202 with minimal adverse affect from the air stream 270 following the sub-sample 204 into the drum 202. In one embodiment, the angle 210 is 22.5 degrees from vertical, which has been found to work well with the conventional HVI 102. In the illustrated embodiment the end portion of the tube 206 has a longitudinal axis that intersects the rotational axis of the drum 202 and is perpendicular to the rotational axis of the drum 202.

In the illustrated embodiment, the tube 206 includes a sensor 274 that detects the passing of the sub-sample 204 toward the sample drum 202. The sensor 274 is connected to the controller 120, which uses the output from the sensor 274 to control the air flow through the delivery tube sub-system 106 and, in particular, the pipe or tube 206. The sensor 274 is positioned in the system 106 such that the controller 120 turns off the air supply pushing the sub-sample 204 toward the sample drum 202. In one such embodiment the sensor 274 is a detector that senses when a laser or directed light beam is broken by the presence of the sub-sample 204. In another embodiment, the controller 120 turns off the air supply pushing the sub-sample 204 toward the sample drum 202 based on a timing signal from an event that corresponds to a known position of the sub-sample 204 in either the CATS 104, an automatic conveying system, or the delivery tube sub-system 106. For example, the initiation of the air stream 270 moving the sub-sample 204 is an event that starts a timer that shuts down the air stream 270 after a certain time has elapsed, where the certain time is the time required for the sub-sample 204 to travel to the end of the tube 206.

The illustrated embodiment shows the end of the tube 206 including a dissipater or series of holes 208 that dissipates the air volume and pressure as the sub-sample 204 reaches the end and exits from the tube 206. The holes 208 allow the air stream 270 to disperse and dissipate, thereby reducing the velocity of the air stream 270 exiting the tube 206 in the same direction as the sub-sample 204 is exiting. In this way the sub-sample 204 is not followed by a blast of air that potentially disperses the sub-sample 204, rendering it unsuitable for testing or otherwise disrupting testing in the HVI 102. In one such embodiment, the holes 208 are regularly spaced around the circumference of the tube 206, with each circumferential row offset from the adjacent row of holes 208. In another embodiment the tube 206 does not include the holes 208.

The air chamber sub-system 108 includes a chamber or box 212 that fits and mates to the bottom of the housing of the sample drum 202. In one embodiment the chamber 212 includes one or more transparent panels that allow visual observation of anything that has been drawn into the chamber.

In the illustrated embodiment a venturi vacuum pump 216 draws a vacuum through a pipe 214 connected to the chamber 212. The venturi pump 216 exhausts through a discharge pipe 218 that flows to a trash or recovery system. The air supply line 132 to the venturi pump 216 is controlled by a valve 222 that discharges pressurized air through the line 220 going to the venturi vacuum pump 216. The controller 120 outputs a control signal 124 to the air chamber sub-system 108 for controlling the valve 222. In one embodiment, the valve 222 is a solenoid valve and the signal 124 energizes the solenoid to open the normally closed valve 222 when a vacuum is desired to be generated. Those skilled in the art will recognize that pumps 216 other than a venturi vacuum pump can be used without departing from the spirit and scope of the present invention.

The sample drum 202, or its drive mechanism, includes an actuator 224 for a proximity sensor 226 that has a signal line 142 that communicates with the controller 120. For example, the actuator 224 is a magnet and the sensor 226 is responsive to the magnet 224, informing the controller 120 when the magnet 224 is proximate the sensor 226. The actuator 224 is positioned such that the drum 202 is in position under the sub-sample delivery tube 206 to receive the sub-sample 204 from the tube 206. When the sample drum 202 is in position, the sensor 226 is triggered by the actuator 224 and the valve 222 is opened by a signal 124 from the controller. The valve 222 is opened at the time that the sub-sample 204 is being delivered from the sub-sample delivery tube sub-system 106. In this way a vacuum is applied to the chamber 212, thereby helping to draw the sub-sample 204 into the sample drum 202 and removing the excess air introduced by the air stream 270 pushing the sub-sample 204 into the sample drum 202.

The sub-sample air-knife extraction sub-system 110 aids in the removal of the sub-sample 204 from the sample drum 202 after the sub-sample 204 has been processed in the sample drum 204 by the HVI 102. The air-knife sub-system 110 includes a nozzle that ejects multiple air streams 234 into the sample drum 202. The air streams 234 are positioned to coincide with openings in the sample plate in the sample drum 202 so that the sub-sample 204 is pushed away and dislodged from the sample plate. The multiple air streams 234 ensure that the sub-sample 204 disengages from the sample plate in the drum 202 in as few pieces as possible, as one sample without the fibers separating.

The air knife 232 is activated by an air line 236 that is pressurized through a valve 238. The controller 120 outputs a control signal 126 to the sub-sample air-knife extraction sub-system 110 for controlling the valve 238. In one embodiment, the valve 238 is a solenoid valve and the signal 126 energizes the solenoid to open the normally closed valve 238 when a sub-sample 204 is to be removed from the sample drum 202.

The sample drum 202, or its drive mechanism, includes an actuator 244 for a proximity sensor 242 that has a signal line 142 that communicates with the controller 120. For example, the actuator 244 is a magnet and the sensor 242 is responsive to the magnet 242, informing the controller 120 when the magnet 242 is proximate the sensor 242. The actuator 244 is positioned such that the sample plate in the drum 202 is in position under the air-knife 232 so that the air streams 234 will engage the openings in the sample plate. When the sample plate is in position, the sensor 242 is triggered by the actuator 244 and the valve 238 is opened by a signal 126 from the controller.

The autoMIC transfer tube sub-system 112 captures the sub-sample 204 after it is released by the air-knife 232 and applies an air jet to the sub-sample 204 to speed the sub-sample 204 on its way to the autoMIC test station in the HVI 102. The transfer tube sub-system 112 includes a funnel chamber 252, a first transfer tube 254, a jet enclosure 256, and a second transfer tube 258. The funnel chamber 252 is below the sample drum 202 under the air-knife 232. The funnel chamber 252 receives the sub-sample 204 after it is released from the sample plate. The sub-sample 204 is pulled into the first transfer tube 254 by a suction in the tube 254. At the same time the sub-sample air-knife extraction sub-system 110 is actuated to release the sub-sample 204, the valve 262 is actuated by a control signal 128 from the controller 120. With the valve 262 open, the line 260 is pressurized and the pressurized air feeds a jet in the jet enclosure 265. The air jet from the line 260 assists the negative pressure in the tube 254, thereby drawing the sub-sample 204 to the jet enclosure 256, and the air jet pushes the sub-sample 204 through the second transfer tube 258 to the autoMIC test station. In this way the sample drum 202 is ready to receive the next sub-sample 204 for testing with no fibers from the previous sub-sample 204 contaminating the sample drum 202.

Figure 3:
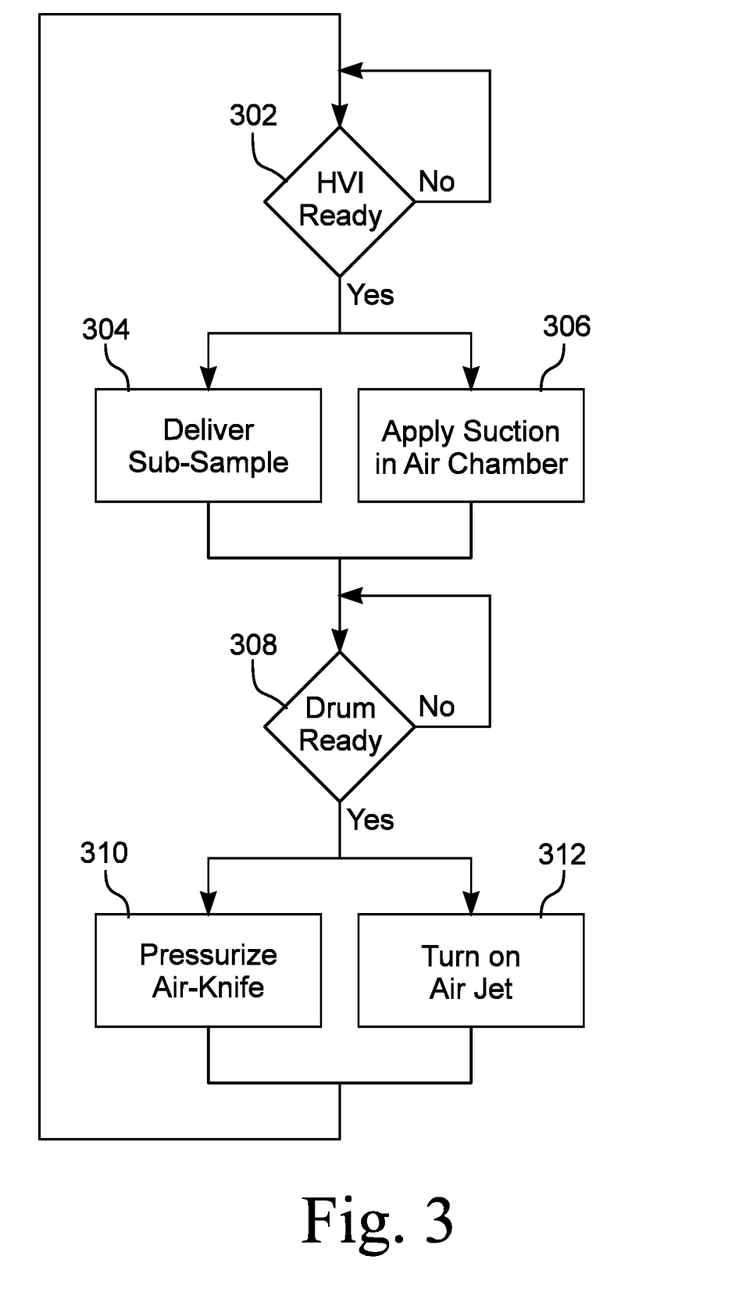
FIG. 3 is a functional flow diagram showing the operation of the automated HVI system.

FIG. 3 illustrates a functional flow diagram showing the operation of the automated HVI system 100. The flow diagram describes the steps for processing a sub-sample 202 with respect to the sample drum 202 of an HVI 102.

The first step 302 is to determine if the HVI 102 is ready to receive a sub-sample 202. If not, the step 302 loops or otherwise waits until the HIV 102 is ready. If the HVI 102 is ready to receive a sub-sample 204, two steps 304, 306 occur simultaneously. The step 304 of delivering a sub-sample 204 through the sub-sample delivery tube sub-system 106 occurs at the same time as the step 306 of applying suction in the air chamber 212 of the air chamber sub-system 108. Referring to FIG. 2, the air stream 270 flows at the same time valve 222 is opened by signal 124. As part of the step 304 of delivering the sub-sample 204, the air supply pushing the sub-sample 204 toward the sample drum 202 is turned off at a selected time to ensure that the sub-sample 204 is not dispersed as it engages the sample drum 202.

After the steps 304, 306 of delivering the sub-sample 202 and applying suction to the air chamber 212 are completed, the next step 308 is to wait until the sample drum 202 is ready to release the sub-sample 204. Once the sub-sample 204 is in the drum 202, the HVI 102 performs operations on the sub-sample 204. After the operations requiring the sample drum 202 are completed, the sample drum 202 is ready to release the sub-sample 204.

When the sample drum 202 is ready to release the sub-sample 204, two steps 310, 312 occur simultaneously. In another embodiment, the steps 310, 312 are controlled independently to accommodate specific configurations. The step 310 of pressurizing the air-knife 232 occurs at the same time as the step 312 of turning on the air jet for the autoMIC transfer tube sub-system 112. In this way the sub-sample 204 is released from the sample drum 202 and moved along to the next location where it is to be tested or discarded.

After the steps 310, 312 of pressurizing the air-knife 232 and turning on the air jet in the jet enclosure 256 are completed, the process loops to the step 302 of determining if the HVI 102 is ready to receive a sub-sample 202. In this way the HVI system 100 continuously processes a series of sub-samples 204 provided by the CATS system 104 or otherwise delivered to the HVI system 100, such as by manual plucking and automatic conveying.

Figure 4:
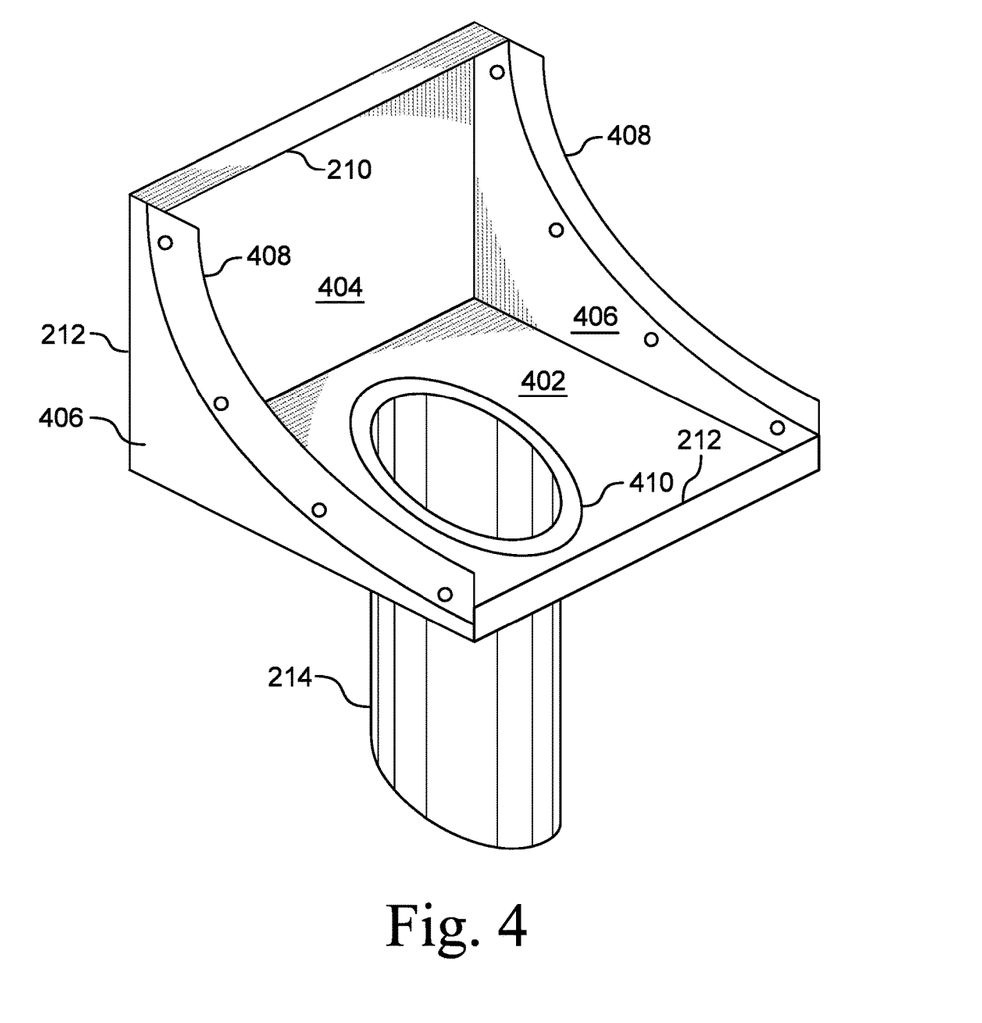
FIG. 4 is an isometric view of one embodiment of a sample drum air chamber.

FIG. 4 illustrates an isometric view of one embodiment of a sample drum air chamber 212. The air chamber 212 mates to the bottom of the housing for the sample drum 102. The chamber 212 includes a bottom plate 402 that supports a front plate 404 and a pair of side plates 406. The side plates 406 have a contoured edge that conforms to the shape of the sample drum housing. Attached to each side plate 406 is a side skirt 408. The side skirts 408 are a flexible, resilient material that forms a seal between the air chamber sub-system 108 and the chamber containing the sample drum 202. Completing the seal to the sample drum chamber are two cross plates 210, 212 that fill the gap between the sample drum chamber and the front and bottom plates 404, 402, respectively.

The bottom plate 402 has a flanged opening 410 that provides passage for the pipe 214 extending to the pump 216. The pump 216 or other vacuum system creates a negative air pressure in the air chamber 212, which aids in drawing the sub-sample 204 into the sample drum 202 from the sub-sample delivery tube sub-system 106.

Figure 5:
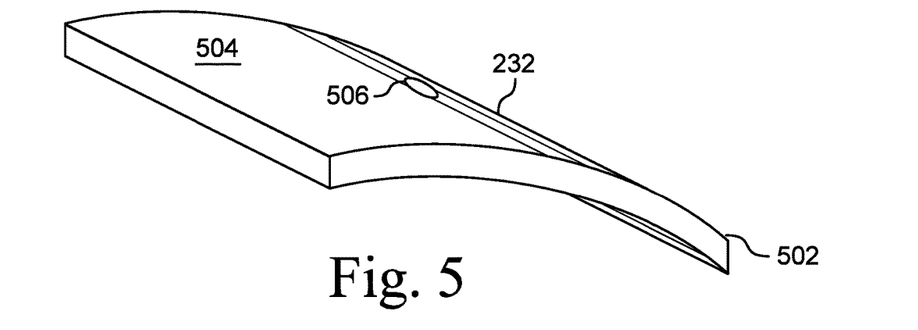
FIG. 5 is an isometric view of one embodiment of an air-knife.
Figure 6:
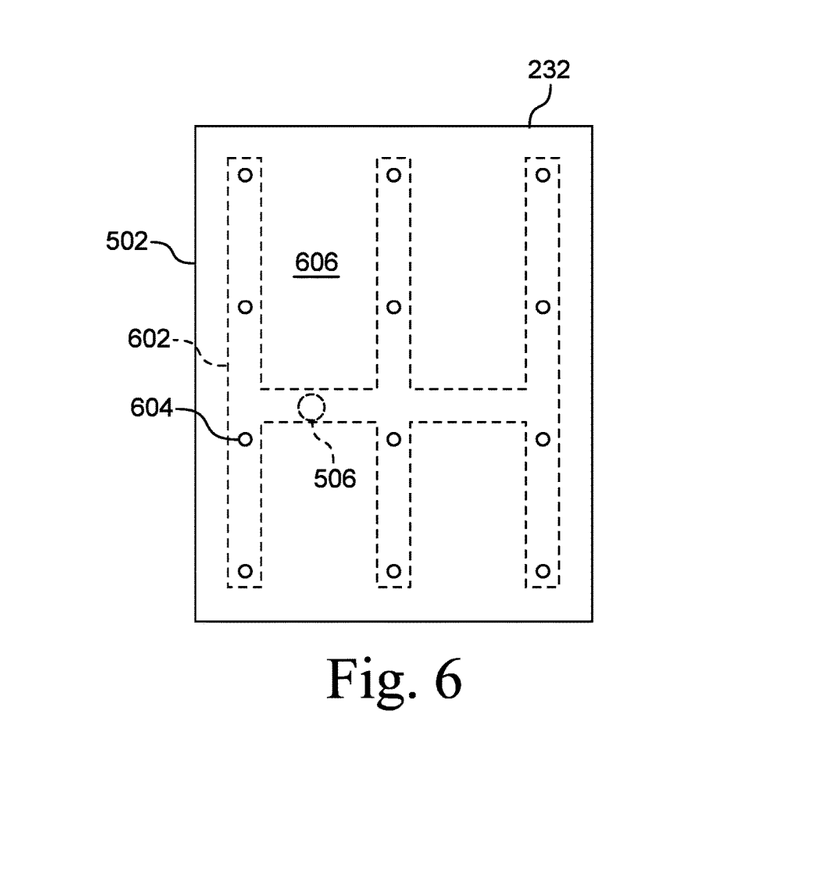
FIG. 6 is a bottom plan view of the air-knife shown in FIG. 5.

FIG. 5 illustrates an isometric view of one embodiment of an air-knife 232. FIG. 6 illustrates a bottom plan view of the air-knife 232 shown in FIG. 5. The air-knife 232 is a curved plate 502 that conforms to the cylindrical shape of the sample drum 202. The bottom surface 606 of the air-knife 232 is positioned a short distance away from the sample drum 202 such that the drum 202 is free to rotate without contacting the air-knife 232.

The air-knife 232 includes air tunnels 602 that are embedded in the plate 502. The air tunnels 602 have capillaries that terminate in exit ports 604 on the surface 606 of the air-knife 232 adjacent to the sample drum 202. The ports 604 are orifices that are spaced apart to coincide with the spacing of at least some of the openings in the sample plate in the sample drum 202. The ports 604 define the air streams 234 that are directed toward the openings in the sample plate in the sample drum 202.

An air inlet port 506 connects the air tunnels 602 to the air line 236 providing pressurized air to the air-knife 232 such that the air is controlled and regulated to not over-excite the fibers leaving the sample drum 202. In the illustrated embodiment, the inlet port 506 is on the side 504 of the plate 502 away from, or opposite, the sample drum 202.

Figure 7:
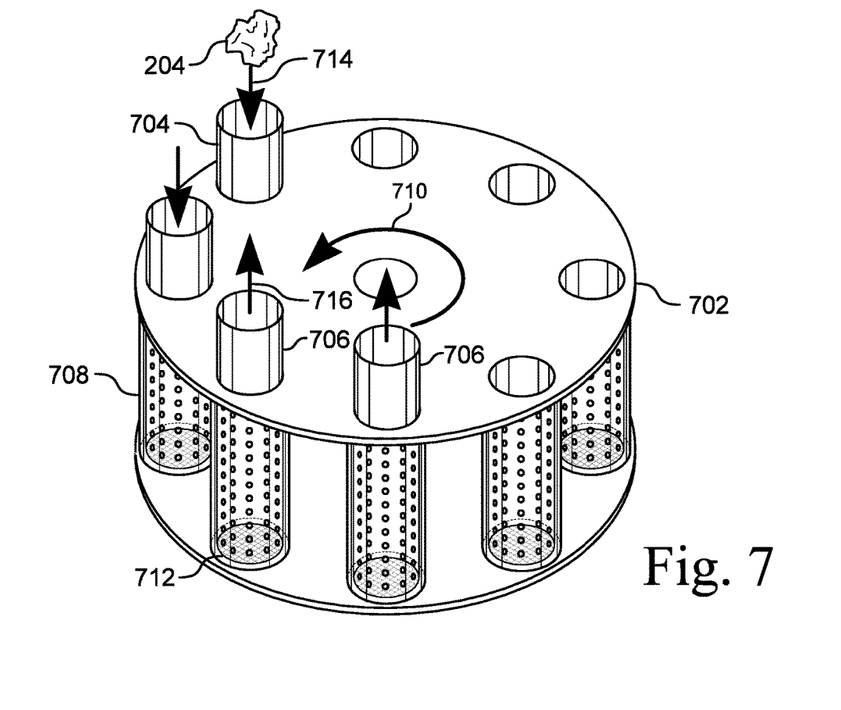
FIG. 7 is an isometric view of a carousel for manual plucking and automatic conveying.

FIG. 7 illustrates an isometric view of one embodiment of a carousel 702 for manual plucking and automatic conveying of sub-samples 204. The illustrated carousel, or indexer, 702 is a type used in a CATS 104. The carousel 702 includes multiple sub-sample carriers 708 for conditioning sub-samples 204 before being tested. The carousel 702 rotates 710 to position selected sub-sample carriers 708 under the intake tubes 704 and the exhaust tubes 706.

FIG. 7 illustrates a sub-sample 204 that was manually plucked from a primary sample and is about to be manually inserted 714 into an intake tube 704 where the sub-sample 204 will be drawn into a sub-sample carrier 708. The sub-sample 204 is drawn through the intake tube 704 and into the sub-sample carrier 708, where the sub-sample 204 is held against a screen 712 at the bottom of the sub-sample carrier 708. Conditioned air is drawn through the sub-sample carrier 708 to condition the sub-sample 204. After the sub-sample 204 is conditioned, a blast of air from the bottom pushes the sub-sample 204 out of the sub-sample carrier 708 into the exhaust tube 706, where the sub-sample 204 moves in a direction 716 away from the sub-sample carrier 708. The sub-sample 204 is routed from the exhaust tube 706 to the delivery tube sub-system 106, which includes the pipe or tube 206 that connects to the sample drum 202. The air moving through the exhaust tube 706 moves the sub-sample 204 in a direction 716 away from the sub-sample carrier 708 as it is conveyed toward the sample drum 202.

Figure 8:
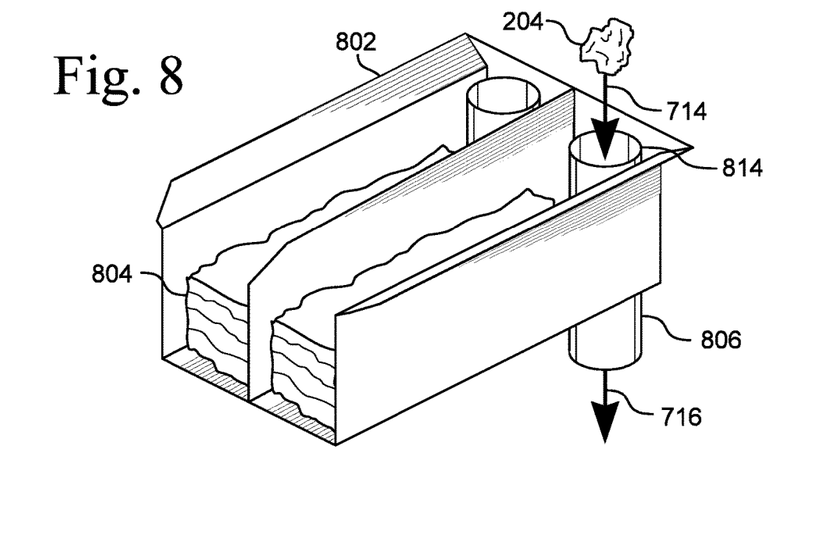
FIG. 8 is an isometric view of a sample carrier with sub-sample receivers.

FIG. 8 illustrates an isometric view of one embodiment of a sample carrier 802 with sub-sample receivers 814 suitable for manual plucking and automatic conveying of sub-samples 204. The sample carrier 802 includes a pair of bins that hold a pair of primary samples 804. At one end of each bin is a receiver or intake tube 814.

The sample carrier 802 typically moves along a conveyor to different stations. At one station where the intake tubes 814 are positioned over transfer tubes 806, a technician manually plucks a sub-sample 204 from one primary sample 804 and deposits the sub-sample 204 into the corresponding intake tube 814, where the sub-sample 204 is drawn downward 714 by a negative pressure below the sample carrier 802. The sub-sample 204 moves downward 714 through the intake tube 814 and into a transfer tube 806. The sub-sample 204 is routed from the transfer tube 806 to the delivery tube sub-system 106, which includes the pipe or tube 206 that connects to the sample drum 202. The air moving through the transfer tube 806 moves the sub-sample 204 in a direction 716 away from the sample carrier 802 as it is conveyed toward the sample drum 202.

In another embodiment, the manual plucking and automatic conveying of the sub-sample 204 occurs when the sample carrier 802 is at two stations. In this embodiment the sample carrier 802 has a receiver or intake tube 814 that has a screen 712 at the bottom. The first station has a plenum positioned under the intake tubes 814 and the plenum is maintained with a negative pressure. The second station has a transfer tube 806 positioned above each intake tube 814. At the first station the sub-sample 204 is plucked from the primary sample 804 and dropped into the intake tube 814, where the sub-sample 204 is drawn into the tube 804 by the negative pressure in the plenum under the tube 814. The sub-sample 204 is captured by the screen 712 in the intake tube 814. In one such embodiment, conditioned air is drawn into the intake tube 814 and through the sub-sample 204, thereby conditioning the sub-sample 204. The sample carrier 802 is moved to a second station where the captured sub-sample 204 moves from the intake tube 814 into the associated transfer tube 806 by a moving air stream in the tubes 814, 806.

The automated HVI system 100 includes various functions. The function of delivering a sub-sample 204 to a sample drum 202 is implemented, in one embodiment, by the sub-sample delivery tube sub-system 106, which includes a tube 206 that pneumatically moves a sub-sample 204 to the drum 202.

The function of applying a vacuum to the housing of the sample drum 202 is implemented, in one embodiment, by an air chamber sub-system 108. In this way the sub-sample 204 is drawn from the delivery tube 106 to the sample drum 202.

The function of removing the sub-sample 204 from the sample drum 202 is implemented, in one embodiment, by the air-knife sub-system 110. The air-knife sub-system 110 directs air jets 234 toward the sub-sample 204, thereby dislodging the sub-sample 204 from the drum 202 for transport to the next stage.

The function of capturing and transferring the released sub-sample 204 is implemented, in one embodiment, by the transfer tube sub-system 112.

The function of capturing the released sub-sample 204 is implemented, in one embodiment, by the negative pressure in the funnel chamber 252 of the transfer tube sub-system 112. The sub-sample 204 is captured by being pulled into the funnel chamber 252 and the connected first transfer tube 254 by a suction in the tube 254.

The function of transferring the released sub-sample 204 is implemented, in one embodiment, by an air jet pushing the sub-sample 204 through the second transfer tube 258 to the test station.

The function of ensuring all fibers are removed from the sample drum 202 is implemented, in one embodiment, by the air-knife sub-system 110 and the transfer tube sub-system 112.

From the foregoing description, it will be recognized by those skilled in the art that apparatus for automating an HVI 102 has been provided. In one embodiment, a sub-sample delivery tube sub-system 106 and an air chamber sub-system 108 provide for delivery of an automated sub-sample 204. In one such embodiment the two sub-systems 106, 108 work in tandem. In other embodiments the sub-systems 106, 108 are installed individually with the installed sub-system 106, 108 aiding in the delivery of the sub-sample 204.

In another embodiment, an air-knife sub-system 110 and an autoMIC transfer tube sub-system 112 provide for release of the automated sub-sample 204 after the HVI 102 completes its operations on the sub-sample 204 in the sample drum 202. In one such embodiment the two sub-systems 110, 112 work in tandem. In other embodiments the sub-systems 110, 112 are installed individually with the installed sub-system 110, 112 aiding in the delivery of the sub-sample 204. For example, the air-knife sub-system 110 is installed on an HVI 102 and operates to release the sub-sample 204 without the autoMIC transfer tube sub-system 112.

In various embodiments the sub-systems 106, 108, 110, 112 have component parts made of transparent material. The transparent material provides a window into the structure, thereby allowing visualization of the sub-sample 204 and any collected debris or fibers.

While the present invention has been illustrated by description of several embodiments and while the illustrative embodiments have been described in considerable detail, it is not the intention of the applicant to restrict or in any way limit the scope of the appended claims to such detail. Additional advantages and modifications will readily appear to those skilled in the art. The invention in its broader aspects is therefore not limited to the specific details, representative apparatus and methods, and illustrative examples shown and described. Accordingly, departures may be made from such details without departing from the spirit or scope of applicant's general inventive concept.

What is claimed is:

1. An apparatus for automating delivery and extraction of a sub-sample in a high volume instrument where the sub-sample is obtained from a primary sample of cotton, the high volume instrument having a sub-sample drum in a housing, said apparatus comprising:
   a delivery tube positioned to deliver the sub-sample to the sub-sample drum;
   a chamber sub-system configured to draw the sub-sample from said delivery tube onto the sub-sample drum;
   an air knife configured to release the sub-sample from the sub-sample drum;
   a transfer system downstream from the sub-sample drum, said transfer system transporting the sub-sample released by said air knife away from the sub-sample drum; and
   a controller operable to perform the following steps:
   a) determine that the high volume instrument is ready to receive the sub-sample;
   b1) when the high volume instrument is ready to receive, deliver the sub-sample through said delivery tube to the sub-sample drum, and
   b2) at the same time as step b1), applying a negative pressure to said air chamber sub-system;
   c) wait until the high volume instrument is ready to release the sub-sample from said sub-sample drum;
   d1) when the high volume instrument is ready to release, apply a pressurized gas to said air knife, and
   d2) at the same time as step d1), apply a negative pressure to an intake of said transfer system.

2. The apparatus of claim 1 wherein said delivery tube has a distal end portion oriented at approximately 22.5 degrees from vertical.

3. The apparatus of claim 1 further including a supply of pressurized gas connected to said delivery tube such that the sub-sample is pushed through a distal end of said delivery tube.

4. The apparatus of claim 3 wherein said delivery tube has a distal end portion with a plurality of openings configured as a dissipater that reduces an exit velocity of the sub-sample exiting said delivery tube.

5. The apparatus of claim 1 wherein said chamber sub-system applies a negative pressure to the housing containing the sample drum, and said negative pressure drawing the sub-sample into the housing from said delivery tube.

6. The apparatus of claim 1 wherein said air knife includes a plate with a plurality of orifices configured to be connected to a gas supply, said plate conforming to a cylindrical shape of the sub-sample drum, and said orifices positioned to direct jets of gas toward a surface of the sub-sample drum such that the sub-sample is released from the sub-sample drum when a pressurized gas exits said plurality of orifices.

7. The apparatus of claim 1 wherein said transfer system includes a chamber connected to the housing of the sub-sample drum, said chamber configured to draw in the sub-sample that said air knife releases from the sub-sample drum when a negative pressure is applied to said chamber.

8. The apparatus of claim 1 further including a sensor responsive to a presence of the sub-sample, and said sensor providing a signal to said controller whereby said controller is operable to turn off a gas flow in said delivery tube upon detection of the sub-sample.

9. An apparatus for automating delivery and extraction of a sub-sample in a high volume instrument having a sub-sample drum in a housing, said apparatus comprising:
- a delivery tube configured to deliver the sub-sample to the sub-sample drum;
- a chamber sub-system configured to be positioned adjacent to the housing containing the sample drum, said chamber sub-system configured to have a sealed pneumatic connection with the housing, said chamber sub-system includes a skirt attached to an opening in a chamber, said skirt having a distal edge that is contoured to conform to the housing of the sub-sample drum when said chamber sub-system is positioned adjacent the housing; and
- a controller operable to apply a positive pressure to said delivery tube to push the sub-sample out a distal end of said delivery tube and apply a negative pressure to the housing containing the sub-sample drum whereby the sub-sample is drawn and held against the sub-sample drum.

10. The apparatus of claim 9 wherein said delivery tube has a distal end portion configured to have an orientation of approximately 22.5 degrees from vertical.

11. The apparatus of claim 9 wherein said delivery tube has a distal end portion with a plurality of openings configured as a dissipater that reduces an exit velocity of the sub-sample exiting said delivery tube.

12. The apparatus of claim 9 further including a sensor responsive to a presence of the sub-sample, and said sensor providing a signal to said controller whereby said controller is operable to turn off a gas flow in said delivery tube upon detection of the sub-sample.

13. The apparatus of claim 9 wherein said controller is operable to turn off a gas flow in said delivery tube a selected time after an initiating event, said selected time corresponding to a time for the sub-sample to travel to a distal end of said delivery tube that is configured to be adjacent the sub-sample drum.

14. The apparatus of claim 9 further including an air knife and a transfer system, said air knife configured to release the sub-sample from the sub-sample drum, and said transfer system downstream from the sub-sample drum, said transfer system transporting the sub-sample released by said air knife away from the sub-sample drum, whereby said controller is operable to apply a pressurized gas to said air knife to release the sub-sample from the sub-sample drum and to apply a negative pressure to an intake of said transfer system such that the sub-sample is released from the sub-sample drum and transported away from the sub-sample drum.

15. The apparatus of claim 14 wherein said air knife includes a plate with a plurality of orifices configured to be connected to a gas supply, said plate conforming to a cylindrical shape of the sub-sample drum, and said orifices configured to direct gas jets toward a surface of the sub-sample drum.

16. An apparatus for automating delivery and extraction of a sub-sample in a high volume instrument having a sub-sample drum in a housing, said apparatus comprising:
- an air knife configured to release the sub-sample from the sub-sample drum, said air knife including a plate with a plurality of orifices configured to be connected to a gas supply, said plate conforming to a cylindrical shape of the sub-sample drum, and said orifices configured to be positioned to direct jets of gas toward a surface of the sub-sample drum such that the sub-sample is released from the sub-sample drum when a pressurized gas exits said plurality of orifices;
- a transfer system having an intake configured to attach to the housing of the sub-sample drum, said transfer system configured to transport the sub-sample released by said air knife; and
- a controller operable to apply a pressurized gas to said air knife and apply a negative pressure to said intake of said transfer system whereby said sub-sample is released from the sub-sample drum and transported away from the sub-sample drum.

17. The apparatus of claim 16 wherein said intake is a chamber configured to be connected to the housing of the sub-sample drum, said chamber configured to draw in the sub-sample that said air knife releases from the sub-sample drum when a negative pressure is applied to said chamber.

18. The apparatus of claim 16 further including a delivery tube and a chamber sub-system, said delivery tube configured to deliver the sub-sample to the sub-sample drum, and said chamber sub-system configured to be connected to the housing containing the sample drum whereby said controller is operable to apply a positive pressure to said delivery tube to push the sub-sample out a distal end of said delivery tube and to apply a negative pressure from said chamber sub-system to the housing containing the sample drum whereby the sub-sample is drawn and held against the sub-sample drum.

* * * * *